United States Patent [19]

Terada et al.

[11] Patent Number: 4,485,202
[45] Date of Patent: Nov. 27, 1984

[54] ISOCYANURIC ACID ESTER STABILIZER

[75] Inventors: Yutaka Terada, Nishinomiya; Shinichi Yachigo, Toyonaka; Tamaki Ishii, Suita, all of Japan

[73] Assignee: Sumitomo Chemical Company, Limited, Osaka, Japan

[21] Appl. No.: 420,081

[22] Filed: Sep. 20, 1982

[30] Foreign Application Priority Data

Sep. 25, 1981 [JP] Japan .................. 56-152530

[51] Int. Cl.³ .................. C08K 5/34; C07D 251/34
[52] U.S. Cl. .................. 524/101; 252/403; 524/305
[58] Field of Search .......... 524/101; 544/221; 560/75, 240; 252/403

[56] References Cited

U.S. PATENT DOCUMENTS

| | | | |
|---|---|---|---|
| 3,707,542 | 12/1972 | Steinberg et al. | 524/101 |
| 3,763,093 | 10/1973 | Kletecka et al. | 524/101 |
| 3,894,016 | 7/1975 | Habermeier et al. | 544/221 |
| 4,069,242 | 1/1978 | Gurgiolo | 560/240 |
| 4,385,143 | 5/1983 | Yachigo et al. | 524/101 |

FOREIGN PATENT DOCUMENTS

| | | |
|---|---|---|
| 2201793 | 8/1972 | Fed. Rep. of Germany . |
| 1367207 | 9/1974 | United Kingdom . |

*Primary Examiner*—Veronica P. Hoke
*Attorney, Agent, or Firm*—Stevens, Davis, Miller & Mosher

[57] ABSTRACT

An isocyanuric acid derivative useful as a stabilizer for organic substances, which is represented by the general formula

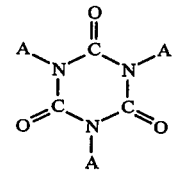

wherein A represents

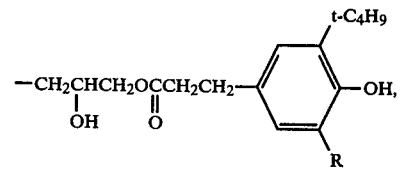

R being an alkyl, cycloalkyl, aryl or aralkyl group having 1 to 8 carbon atoms; a process for preparing same; organic substances stabilized with same; and a method of stabilizing an organic substance.

14 Claims, No Drawings

ISOCYANURIC ACID ESTER STABILIZER

This invention relates to an isocyanuric acid derivative represented by the general formula

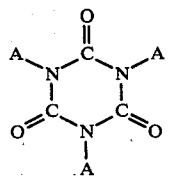
(I)

wherein A represents

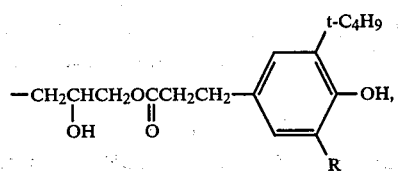

R being an alkyl, cycloalkyl, aryl or aralkyl group having 1 to 8 carbon atoms; a process for preparing same; a stabilizer for organic compounds comprising same as active constituent; and a method for stabilizing an organic substance. The isocyanuric acid derivative represented by the general formula (I) is a novel compound not found in the literature but first synthesized by the present inventors.

As is well known, various organic substances including synthetic resins such as polyolefin, ABS resin, polystyrene, high-impact polystyrene, polyamide, polyacetal, and ethylene-propylene copolymer, natural and synthetic rubbers such as butadiene rubber, isoprene rubber, isoprene-isobutylene copolymer rubber, styrene-butadiene copolymer rubber, acrylonitrile-butadiene copolymer rubber, and EPDM, and petroleum products such as lubricating oil and fuel oil are liable to degradation when exposed to the action of heat, light, or oxygen. It is also known that various stabilizers are incorporated in these organic substances to protect them from such degradation. The conventional stabilizers, however, have a defect of insufficient thermal stability and when exposed to elevated temperatures for a long time, the stabilizing effect becomes gradually decreased.

The present invention is an outcome of the extensive study directed to the development of a compound highly effective in protecting the above-mentioned organic substances from degradation.

The present isocyanuric acid derivative represented by the general formula (I) is prepared by the reaction of triglycidyl isocyanurate with a propionic acid derivative represented by the general formula

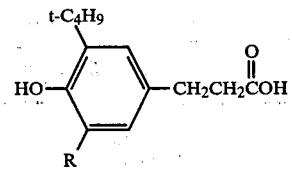
(II)

wherein R is as defined above and exemplified by methyl, ethyl, n-propyl, isopropyl, n-butyl, t-butyl, hexyl, octyl, 2-ethylhexyl, cyclopentyl, cyclohexyl, cycloheptyl, 1-methylcyclohexyl, phenyl, benzyl, and methylbenzyl. The reaction is generally carried out in an organic solvent in the presence of a basic catalyst.

The organic solvents suitable for the reaction include aromatic hydrocarbons such as benzene, toluene, and xylenes; aliphatic hydrocarbons such as n-hexane, cyclohexane, and n-heptane; ketones such as acetone, methyl ethyl ketone, and methyl isobutyl ketone; esters such as ethyl acetate and butyl acetate; halohydrocarbons such as chloroform and carbon tetrachloride; and aprotic polar solvents such as dimethylformamide and dimethyl sulfoxide. Alcohols are unsuitable, because they react with the starting material, triglycidyl isocyanurate, forming by-products.

Suitable catalysts are tertiary amines such as triethylamine and tributylamine; quaternary ammonium salts such as trimethylbenzylammonium hydroxide and tetramethylammonium hydroxide; imidazoles represented by 2-ethyl-4-methylimidazole; and alkali metal alkoxides such as potassium methoxide and sodium methoxide. The reaction temperature is 30° to 200° C., preferably 50° to 150° C. The molar ratio between the starting materials, that is, triglycidyl isocyanurate and a propionic acid derivative, is from 1:2.5 to 1:3.5. After completion of the reaction, the reaction product is separated in a customary manner and purified by recrystallization, washing with a solvent, or other known means.

The isocyanuric acid derivative of the present invention is effective as a stabilizer for various organic substances including synthetic resins such as polyolefin (e.g. polyethylene or polypropylene), ABS resin, polystyrene, high-impact polystyrene, and polyamide; synthetic rubbers such as butadiene rubber, isoprene rubber, styrene-butadiene copolymer rubber and EPDM; and petroleum products such as lubricating oil and fuel oil.

Although variable depending upon the type of organic substance being stabilized, the amount of the present isocyanuric acid derivative to be added is generally in the range of from about 0.001 to about 5, preferably from about 0.01 to about 2, parts by weight for 100 parts by weight of the organic substance. The incorporation of the compound in an organic substance is performed in a customary manner.

Although effective by itself for the stabilization of organic substances, the present isocyanuric acid derivative can be used, if necessary, in combination with other additives. It exhibits a synergistically enhanced stabilizing effect especially when used in combination with peroxide-decomposing agents of the organosulfur type such as thiodipropionate esters (e.g. dilauryl 3,3'-thiodipropionate, dimyristyl 3,3'-thiodipropionate, and distearyl 3,3'-thiodipropionate) represented by the general formula

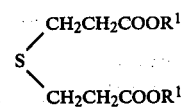
(III)

wherein $R^1$ represents an alkyl group having 12 to 20 carbon atoms, or pentaerythritol derivatives (e.g. pentaerythritol tetrakis($\beta$-lauryl thiopropionate) and pentaerythritol tetrakis($\beta$-stearyl thiopropionate)) represented by the general formula

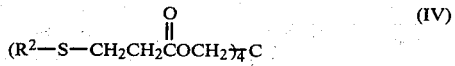

$$(R^2-S-CH_2CH_2COCH_2)_3C \quad \text{(IV)}$$

wherein $R^2$ represents an alkyl group having 4 to 20 carbon atoms. These peroxide-decomposing agents are used preferably in an amount of 0.1 to 10 times the weight of the isocyanuric acid derivative of this invention. The total amount of the isocyanuric acid derivative and the peroxide-decomposing agent used in stabilizing an organic substance is generally 0.01 to 5 parts by weight for 100 parts by weight of the organic substance.

The light stability of the organic substance containing the present isocyanuric acid derivative can be improved by the addition of ultraviolet absorbers or light stabilizers of the hindered amine type such as, for example, 2-hydroxy-4-methoxybenzophenone, 2-hydroxy-4-n-octoxybenzophenone, 2-(2-hydroxy-5-methylphenyl)-benzotriazole, 2-(2-hydroxy-3-t-butyl-5-methylphenyl)-5-chlorobenzotriazole, 2-(2-hydroxy-3,5-di-t-butylphenyl)-5-chlorobenzotriazole, 2-(2-hydroxy-3,5-diamylphenyl)benzotriazole, [2,2'-thiobis-(4-t-octylphenolate)]butylamine nickel salt, 2,2,6,6-tetramethyl-4-piperidinyl benzoate, bis(2,2,6,6-tetramethyl-4-piperidinyl)sebacate, 2-(3,5-di-t-butyl-4-hydroxybenzyl)-2-n-butylmalonate, 1-[2-{3-(3,5-di-t-butyl-4-hydroxyphenyl)-propionyloxy}ethyl]-4-[3-(3,5-di-t-butyl-4-hydroxyphenyl)propionyloxy]-2,2,6,6-tetramethylpiperidine, and dimethyl succinate-1-(2-hydroxyethyl)-4-hydroxy-2,2,6,6-tetramethylpiperidine polycondensate. The color of the stabilized organic substance can be improved by the addition of phosphite antioxidants such as, for example, distearylpentaerythritol diphosphite, tris(2,4-di-t-butylphenyl)phosphite, tris(2-t-butyl-4-methylphenyl)phosphite, and bis(2,4-di-t-butylphenyl)pentaerythritol diphosphite, tetrakis(2,4-di-t-butylphenyl)-4,4'-biphenylene diphosphite. In addition to the above, the following materials may be used depending on practical purposes: plasticizers, metal deactivating agents, metallic soaps, nucleating agents, lubricants, antistatics, flame retardants, pigments, fillers, petroleum additives (e.g. corrosion inhibitors, rust preventives, pour point depressants, defoamers, detergent dispersants, and extreme pressure additives), and metal chelating agents.

When used together with said other additives, these additives can be used as a mixture with the isocyanuric acid derivative of this invention.

The invention is further illustrated below with reference to Examples.

EXAMPLE 1

A mixture of 4.17 g (0.015 mole) of 3,5-di-t-butyl-4-hydroxyphenylpropionic acid, 1.49 g (0.005 mole) of triglycidyl isocyanurate, 0.1 g (0.001 mole) of triethylamine, and 40 g of toluene was heated at 110° to 112° C. for 14 hours to allow the reaction to proceed. The reaction mixture was kept at 80° C. and 50 Torr for 5 hours to recover the solvent and to obtain as the residue 5.6 g (99% yield) of a crude product, pale yellow in color. The crude product was recrystallized from 20 ml of methanol to yield 2.6 g of white powder of 1,3,5-tris{3-[3-(3,5-di-t-butyl-4-hydroxyphenyl)propionyloxy]-2-hydroxypropyl}isocyanuric acid having a melting point of 59°–62° C. (Compound I-1).

| | C % | H % | N % |
|---|---|---|---|
| Elementary analysis: | | | |
| Calculated for $C_{63}H_{93}N_3O_{15}$ | 66.2 | 8.4 | 3.9 |
| Found | 66.8 | 8.2 | 3.7 |
| Mass analysis: | | | |
| Molecular ion peak: | | 1131 | |
| Fragment ion peak: | | 377 | |

EXAMPLE 2

A mixture of 3.54 g (0.015 mole) of 3-methyl-4-hydroxy-5-t-butylphenylpropionic acid, 1.49 g (0.005 mole) of triglycidyl isocyanurate, 0.11 g (0.001 mole) of 2-ethyl-4-methylimidazole, and 40 g of xylene was heated at 130° to 135° C. for 10 hours to allow the reaction to proceed. The reaction mixture was washed with 100 ml of 1% dilute hydrochloric acid, then with 100 ml of water. The organic layer was kept at 80° C. and 50 Torr for 3 hours to remove the solvent, leaving behind 4.7 g (93% yield) of a yellow wax-like crude product. The crude product was recrystallized from 15 ml of methanol to yield 2.3 g of a white powder of 1,3,5-tris{3-[3-(3-t-butyl-5-metyl-4-hydroxyphenyl)propionyloxy]-2-hydroxypropyl}isocyanuric acid having a melting point of 31°–34° C. (Compound I-2).

| | C % | H % | N % |
|---|---|---|---|
| Elementary analysis: | | | |
| Calculated for $C_{54}H_{75}N_3O_{15}$ | 64.0 | 7.8 | 4.3 |
| Found | 64.5 | 7.5 | 4.2 |
| Mass analysis: | | | |
| Molecular ion peak: | | 1005 | |
| Fragment ion peak: | | 335 | |

EXAMPLES 3 TO 7

Various isocyanuric acid derivatives (Compounds I-3, I-4, I-5, I-6 and I-7) were prepared by repeating the procedure of Example 1, except that each of the 3-t-butyl-4-hydroxy-5-(R=substituent)phenylpropionic acids, shown in Table 1, was used in place of the 3,5-di-t-butyl-4-hydroxyphenylpropionic acid. The results obtained were as shown in Table 1.

TABLE 1

| Example No. | Starting material R in formula II | Compound No. | R in formula I | Melting point, °C. | Yield, % | Elementary analysis | | | |
|---|---|---|---|---|---|---|---|---|---|
| | | | | | | | C % | H % | N % |
| 3 | —CH₂CH₂CH₂CH₂CH₂CH₃ | I-3 | Same as in formula II | 38–41 | 45 | Found: Calculated for $C_{69}H_{105}N_3O_{15}$: | 68.2 68.1 | 8.6 8.7 | 3.3 3.5 |
| 4 | —CH₂CHCH₂CH₂CH₂CH₃ with CH₂CH₃ branch | I-4 | | Wax-like | 32 | Found: Calculated for $C_{75}H_{117}N_3O_{15}$: | 69.6 69.3 | 8.8 9.1 | 3.0 3.2 |

TABLE 1-continued

| Example No. | Starting material R in formula II | Compound No. | R in formula I | Melting point, °C. | Yield, % | Elementary analysis | | | |
|---|---|---|---|---|---|---|---|---|---|
| | | | | | | | C % | H % | N % |
| 5 | —⟨CH₃,H cyclohexyl⟩ | I-5 | | 65–69 | 41 | Found: Calculated for C₇₂H₁₀₅N₃O₁₅: | 69.3 69.0 | 8.4 8.5 | 3.1 3.4 |
| 6 | —⟨phenyl⟩ | I-6 | | 68–73 | 38 | Found: Calculated for C₆₉H₈₁N₃O₁₅: | 69.7 69.5 | 6.6 6.9 | 3.2 3.5 |
| 7 | —CH(CH₃)—⟨phenyl⟩ | I-7 | | 40–44 | 43 | Found: Calculated for C₇₅H₉₃N₃O₁₅: | 70.3 70.6 | 7.5 7.3 | 3.0 3.3 |

Below are shown Examples of stabilization tests for organic substances. In Examples, the following compounds were used for comparison.
AO-1 2,6-Di-t-butyl-4-methylphenol
AO-2 n-Octadecyl 3-(3,5-di-t-butyl-4-hydroxyphenyl)-propionate
AO-3 Pentaerythritol tetrakis[3-(3,5-di-t-butyl-4-hydroxyphenyl)propionate]
AO-4 1,3,5-Trimethyl-2,4,6-tris(3,5-di-t-butyl-4-hydroxybenzyl)benzene

EXAMPLE 8

| | Parts by weight |
|---|---|
| Unstabilized polypropylene resin (Sumitomo Noblen FS-200) | 100 |
| Calcium stearate | 0.1 |
| Compound being tested (Table 2) | 0.2 |

The above ingredients were blended together in a mixer for 5 minutes and then milled in molten state on a roller mixing mill at 180° C. The milled mixture was molded in a hot press at 210° C. into a sheet of 1 mm in thickness. Test specimens, 40×40×1 mm, were prepared from the sheet and tested in a Geer oven at 150° C. for the time elapsed before 30% of the surface area of each specimen had become brittle. The results obtained were as shown in Table 2.

TABLE 2

| | | Test compound | 30% Enbrittlement time, hour |
|---|---|---|---|
| Run No. (This invention) | 1 | I-1 | 1100 |
| | 2 | I-2 | 1080 |
| | 3 | I-3 | 980 |
| | 4 | I-4 | 890 |
| | 5 | I-5 | 920 |
| Comparative Run No. | 1 | AO-1 | ≦24 |
| | 2 | AO-2 | 270 |
| | 3 | AO-4 | 640 |
| | 4 | None | ≦20 |

EXAMPLE 9

Stabilization tests were carried out under the same conditions as in Example 8, except that the following compounding recipe was used. The results obtained were as shown in Table 3.

| | Parts by weight |
|---|---|
| Unstabilized polypropylene resin (Sumitomo Noblen FS-200) | 100 |
| Calcium stearate | 0.1 |
| Test compound (Table 3) | 0.05 |
| Dilauryl 3,3'-thiodipropionate (SYAO-1) or pentaerythritol tetrakis-(β-laurylthiopropionate) (SYAO-2) | 0.2 |

TABLE 3

| | | Test compound | 30% Enbrittlement time, hour | |
|---|---|---|---|---|
| | | | SYAO-1 | SYAO-2 |
| Run No. (This invention) | 6 | I-1 | 1550 | 1490 |
| | 7 | I-2 | 2870 | 2900 |
| | 8 | I-3 | 1060 | 1100 |
| | 9 | I-4 | 1090 | 1120 |
| | 10 | I-5 | 1210 | 1350 |
| | 11 | I-6 | — | 2050 |
| | 12 | I-7 | — | 1700 |
| Comparative Run No. | 5 | AO-1 | ≦24 | ≦24 |
| | 6 | AO-2 | 540 | 580 |
| | 7 | AO-4 | 930 | 830 |
| | 8 | None | ≦20 | ≦20 |

EXAMPLE 10

Using an unstabilized polybutadiene rubber containing no antioxidant (JSR BR-01 extracted with acetone to remove the antioxidant), the compounding ingredients of the recipes 1, 2 or 3, shown below, were milled on a roller mill. The resulting rubber was tested for stability against both heat and oxidation as well as discoloration upon heating. The results obtained were as shown in Tables 4 and 5.

The stability against heat and oxidation was evaluated by subjecting the rubber specimen to thermal aging in a Geer oven at 100° C., measuring the gel content (toluene insolubles) at 15-hour intervals, and determining the time elapsed before the gel content had reached 10% by weight (this time span is herein referred to as gel I.P.). The discoloration upon heating was evaluated by the color of the rubber specimen (recipe 1) after heating in a Geer oven at 100° C. for 15, 60, and 120 hours. The rubber compositions of recipes 2 and 3 were evaluated after heating for 30 hours.

RECIPE 1

|  | Parts by weight |
| --- | --- |
| Unstabilized polybutadiene rubber | 100 |
| Test compound (Table 4) | 1 |

RECIPE 2

|  |  |
| --- | --- |
| Unstabilized polybutadiene rubber | 100 |
| Ditridecyl 3,3'-thiodipropionate | 0.25 |
| Test compound (Table 5) | 0.75 |

RECIPE 3

|  |  |
| --- | --- |
| Unstabilized polybutadiene rubber | 100 |
| Pentaerythritol tetrakis(β-lauryl-thio-propionate) | 0.25 |
| Test compound (Table 5) | 0.75 |

TABLE 4

(Recipe 1)

|  |  | Test compound | Gel I.P. (hour) | Color of rubber after heating for | | | |
| --- | --- | --- | --- | --- | --- | --- | --- |
|  |  |  |  | 0 hour | 15 hours | 60 hours | 120 hours |
| Run No. (This invention) | 13 | I-1 | 160 | White | White | White | White |
|  | 14 | I-2 | 125 | " | " | " | " |
|  | 15 | I-3 | 100 | " | " | " | " |
|  | 16 | I-4 | 105 | " | " | " | " |
|  | 17 | I-5 | 100 | " | " | " | " |
|  | 18 | I-6 | 95 | " | " | " | Pale yellow |
|  | 19 | I-7 | 95 | " | " | " | " |
| Comparative Run No. | 9 | A0-1 | 80 | " | White | Yellow | Yellow |
|  | 10 | A0-2 | 35 | " | " | " | " |
|  | 11 | A0-3 | 55 | " | " | Pale yellow | " |
|  | 12 | None | 5 | " | Yellow | Yellow | " |

TABLE 5

|  |  | Test compound | Recipe 2 | | Recipe 3 | |
| --- | --- | --- | --- | --- | --- | --- |
|  |  |  | Gel I.P. (hour) | Color | Gel I.P. (hour) | Color |
| Run No. (This invention) | 20 | I-1 | 180 | White | 210 | White |
|  | 21 | I-2 | 180 | " | 250 | " |
|  | 22 | I-3 | 120 | " | 185 | " |
|  | 23 | I-4 | 130 | " | 190 | " |
|  | 24 | I-5 | 125 | " | 160 | " |
|  | 25 | I-6 | 120 | " | 150 | " |
|  | 26 | I-7 | 115 | " | 155 | " |
| Comparative Run No. | 13 | A0-1 | 90 | " | 100 | Pale yellow |
|  | 14 | A0-2 | 50 | " | 80 | White |
|  | 15 | A0-3 | 85 | " | 100 | " |
|  | 16 | No Additive | 5 | Yellow | 5 | Yellow |

What is claimed is:

1. An isocyanuric acid derivative represented by the general formula

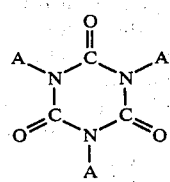

(I)

wherein A represents

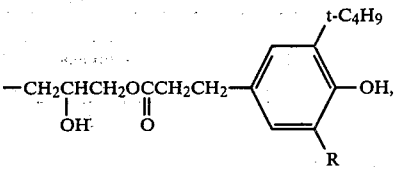

R being an alkyl, cycloalkyl, aryl or aralkyl group having 1 to 8 carbon atoms.

2. An isocyanuric acid derivative according to claim 1, wherein the substituent R in the general formula (I) is an alkyl group having 1 to 8 carbon atoms.

3. An isocyanuric acid derivative according to claim 2, wherein the alkyl group is methyl, t-butyl, n-hexyl or 2-ethylhexyl.

4. An isocyanuric acid derivative according to claim 1, wherein the substituent R in the general formula (I) is 1-methylcyclohexyl, phenyl or α-methylbenzyl.

5. A stabilizer composition for organic substances normally subject to oxidative degradation comprising the isocyanuric acid derivative of claim 1 and a peroxide-decomposing agent of the organosulfur type is jointly used in an amount of 0.1 to 10 times the weight of the isocyanuric acid derivative.

6. A stabilizer according to claim 5, wherein the peroxide-decomposing agent of the organosulfur type is a thiodipropionate ester represented by the general formula

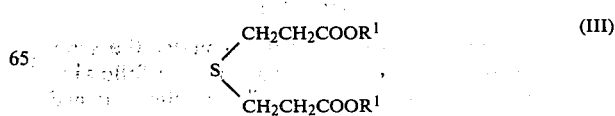

(III)

wherein $R^1$ represents an alkyl group having 12 to 20 carbon atoms, or a petaerythritol derivative represented by the general formula $$(R^2-S-CH_2CH_2\underset{\underset{O}{\|}}{C}OCH_2)_4 C, \quad (IV)$$

wherein $R^2$ represents an alkyl group having 4 to 20 carbon atoms.

7. A stabilized organic substance comprising an organic substance normally subject to oxidative degradation and an isocyanuric acid derivative represented by the general formula (I)

wherein A represents

R being an alkyl, cycloalkyl, aryl or aralkyl group having 1 to 8 carbon atoms, in an amount of 0.001 to 5 parts by weight for 100 parts by weight of the organic substance.

8. A stabilized organic substance according to claim 7, wherein the organic substance further contains a peroxide-decomposing agent of the organosulfur type in an amount of 0.1 to 10 times the weight of the isocyanuric acid derivative represented by the general formula (I) and the total amount of both additives is 0.01 to 5 parts by weight for 100 parts by weight of the organic substance.

9. A stabilized organic substance according to claim 8, wherein the peroxide-decomposing agent of the organosulfur type is a thiodipropionate ester represented by the general formula $$S\underset{\diagdown}{\overset{\diagup CH_2CH_2COOR^1}{\phantom{X}}}_{CH_2CH_2COOR^1}, \quad (III)$$

where $R^1$ represents an alkyl group having 12 to 20 carbon atoms, or a pentaerythritol derivative represented by the general formula $$(R^2-S-CH_2CH_2\underset{\underset{O}{\|}}{C}OCH_2)_4 C, \quad (IV)$$

where $R^2$ represents an alkyl group having 4 to 20 carbon atoms.

10. A stabilized organic substance according to claim 7, 8 or 9, wherein the organic substance is a synthetic resin.

11. A stabilized organic substance according to claim 10, wherein the synthetic resin is a polyolefin.

12. A stabilized organic substance according to claim 23, wherein the polyolefin is polypropylene.

13. A stabilized organic substance according to claim 7, 8 or 9, wherein the organic substance is a synthetic rubber.

14. A stabilized organic substance according to claim 13, wherein the synthetic rubber is a butadiene rubber.

* * * * *